United States Patent [19]

Hernestam et al.

[11] Patent Number: 4,894,221
[45] Date of Patent: Jan. 16, 1990

[54] METHOD OF TREATING PLAQUE USING MORPHOLINE COMPOUNDS

[75] Inventors: Sven E. H. Hernestam; Nils A. Nilsson; Willard Lars-Olof, all of Malmo, Sweden

[73] Assignee: AB Ferrosan, Malmo, Sweden

[21] Appl. No.: 480,399

[22] Filed: Mar. 30, 1983

Related U.S. Application Data

[63] Continuation-in-part of Ser. No. 245,441, Mar. 19, 1981, abandoned.

[51] Int. Cl.$^4$ ............................................. A61K 7/22
[52] U.S. Cl. ................................ 424/54; 514/238.8; 544/170
[58] Field of Search ............ 544/170; 424/54, 248.57; 514/238.8

[56] References Cited

U.S. PATENT DOCUMENTS

| | | | |
|---|---|---|---|
| 1,923,179 | 8/1933 | Ulrich et al. | 544/170 |
| 2,040,039 | 5/1936 | Bruson . | |
| 2,105,828 | 1/1938 | Wilson | 544/170 |
| 2,477,842 | 8/1949 | Wenner | 544/170 |
| 2,921,886 | 1/1960 | Panepinto . | |
| 3,018,222 | 1/1962 | Siemer et al. | 544/170 |
| 3,308,111 | 3/1967 | Braus et al. | 544/170 |
| 3,872,116 | 3/1975 | Gipson | 544/170 |
| 3,926,861 | 12/1975 | Gerecht | 544/173 |
| 4,026,935 | 5/1977 | Brennan et al. . | |
| 4,103,087 | 7/1978 | Brennen | 544/170 |
| 4,117,227 | 9/1978 | Brennan | 544/170 |

FOREIGN PATENT DOCUMENTS 129955 3/1969 Norway .
682160 11/1952 United Kingdom .

*Primary Examiner*—Robert W. Ramsuer
*Attorney, Agent, or Firm*—Scully, Scott, Murphy & Presser

[57] ABSTRACT

Novel morpholino compounds having the general formula

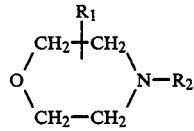

wherein $R_1$ is a straight or branched alkyl group containing 8 to 16 carbon atoms at the 2- or 3-position of the morpholino ring, and $R_2$ is a straight or branched alkyl group containing 2 to 10 carbon atoms, substituted with a hydroxy group except in the alpha-position, the sum of the carbon atoms in the groups $R_1$ and $R_2$ being at least 10 and preferably 10 to 20; and pharmaceutically acceptable salts thereof. Compositions for the treatment of the oral cavity and especially the tooth surfaces containing the novel compound or a salt thereof, preferably from 0.1 to 5% by weight thereof. Use of the compounds to inhibit the formation of dental plaque or remove plaque already formed by application of the compound in an aqueous solution or a composition to the surfaces of the oral cavity, especially the surfaces of the teeth. Processes for the preparation of the compounds.

2 Claims, 2 Drawing Sheets

Fig.1

Fig.2

METHOD OF TREATING PLAQUE USING MORPHOLINE COMPOUNDS

BACKGROUND

The present application is a Continuation-In-Part of the U.S. application Ser. No. 245,441 filed March 19, 1981 now abandoned.

The present invention relates to novel morpholino compounds, processes for the preparation thereof, the use of the compounds in compositions for the treatment of the oral cavity, especially the tooth surfaces, and for the inhibition or removal of dental plaque, and a method of keeping the tooth surface clean.

The novel morpholino derivatives according to this invention are represented by the following general formula:

I wherein $R_1$ is a straight or branched alkyl group containing to 16 carbon atoms at the 2- or 3-position of the morpholino ring, and $R_2$ is a straight or branched alkyl group containing 2 to 10 carbon atoms, substituted with a hydroxy group except in the alpha-position. The sum of the carbon atoms in the groups $R_1$ and $R_2$ is at least 10 and preferably 10 to 20.

The novel compounds of the formula I above have valuable properties for maintaining the oral cavity hygiene since when applied to the tooth surfaces in solution or in a composition they inhibit the formation of dental plaque and also have the ability to remove plaque already formed. For this reason they prevent especially dental caries, gingivitis and parondontitis. The compounds do not exhibit a pronounced antibacterial effect, which is of importance for the maintenance of a normal bacterial status in the oral cavity and in the intestinal tract.

The novel compounds according to the invention can be prepared according to several processes, especially the following:

(a) by alkylating a morpholino derivative having the formula

II wherein $R_l$ is as defined above; with an alkylating agent of the formula $R_2X$   III wherein $R_2$ is as defined above and X is halogen or an hydroxyl group present in $R_2$ is a reactive oxide;

(b) by ring closure of a compound having the general formula

IV wherein $R_l$ is as defined above, X is halogen or an organic sulfonic ester and A represents $CH_2$ groups, one $CH_2$ group being substituted with the group $R_1$; with an amino alkanol of the general formula $NH_2R_2$   V wherein $R_2$ is as defined above;

(c) by reducing a mono- or di-oxo substituted morpholine having the general formula

VII wherein $R_2$ $_{pl\ is\ as\ defined\ above}$, n is 0 or 1, and $R_1$ is as defined above and is at the 2-position when n is 1 and at the 2- or 3-position when n is 0, for the preparation of a compound of formula I;

(d) by starting from a morpholino compound having the general formula

VIII wherein $R_1$ is as defined above and $R_3$ is a straight branched alkyl group containing a group transformable to OH or $CH_2OH$; especially

(d1) by converting a compound of the formula VIII, wherein the group in $R_3$ transformable to OH is halogen, NHAc, OAc, O—alkyl, O—$CH_2 \cdot C_6H_5$; or (d2) by converting a compound of the formula VIII, wherein the group in $R_3$ transformable to $CH_2OH$ is —$COOC_2H_5$, —CN, —CHO; or (d3) $R_3$ represents -$CO(CH_2)_n$—$COOC_2H_5$ (n=0—8).

(Preparation a (1)

The preparation of the compound II, being the starting material in reaction a), can be performed by ring closure of the compound

IX wherein $R_1$ and A are as defined above and R is a hydrogen atom or the group —$CH_2C_6H_5$, according to known methods, such as treatment with 70% $H_2SO_4$ at 100°–150° C., and removal of the -CH by reduction with hydrogen and using, e.g., Pd/C as a catalyst at a pressure of 10 atmospheres in ethanol and at 50° C.

The morpholino compound II is reacted with e.g. halogen alkanols or alkylene oxides in a suitable solvent, such as benzene or toluene. When using halogen alkanols or organic sulfonic esters, the reactions are performed either with an excess of the morpholine or in the presence of another acid-binding agent, such as triethyl amine, potassium carbonate or the like, and preferably at an elevated temperature, e.g. 75°–150° C. in an autoclave. The preparation described above can be used for all substituted morpholines of the general formula I.

Preparation (b)

Thee hydroxyl groups of the dioles having the formula

X wherein $R_1$ and A are as defined above are halogenated with, e.g., $SOCl_2$ to

XI with subsequent ring closure with $H_2NR_2$ (V) at 120°–170° C. in an autoclave. The reaction is performed in the presence of an acid-binding agent such as $K_2CO_3$.

Preparation (c) This reaction is preferably performed using lithium aluminum hydride in diethyl ether or tetrahydrofuran as the reaction medium. The reaction mixture is preferably treated with water and NaOH and the ether solution of the morpholino derivative purified by distillation.

The dioxo derivative of the formula VII is conveniently prepared by treatment of the corresponding substituted acid having the formula

XIII wherein $R_1$ is as defined above, as derivative or anhydride thereof, with a compound of the formula

$NH_2R_2$   V wherein $R_2$ is as defined above. The reaction is conveniently carried out by heating a mixture of the compounds at a temperature of 100°–250° C. in an autoclave for 10–20 hours without the presence of a solvent. The yields usually exceed 75% of those theoretically calculated. This method only produces the 2-substituted morphlino derivatives.

Mono-oxo derivatives having the formulae

XIV or

XV can be prepared from the following substituted halogen acids:

hal-$CH_2CH_2OCHCOOH$ with $R_1$   XVI hal-$CHCH_2OCH_2COOH$ with $R_1$   XVII hal-$CH_2CHOCH_2COOH$ with $R_1$   XVIII wherein $R_1$ is as defined above. Ring closure is carried out under conditions similar to those stated above for the reaction between the compounds XIII and V.

Preparation (d)

The starting compound wherein $R_1$ and $R_3$ are as defined above, is synthesized as described above for preparation (a). (The $NH_2$ groups in the side chain $R_3$ are protected by acetyl groups). The halogen is transformed to 0-acetyl by treatment with AgO-acetyl in acetic acid at 100° C. The acetyl group is removed by hydrolysis with alkali or acid.

The —NH—acetyl group is hydrolyzed to $NH_2$ and the amine group is transformed to hydroxyl by treatment with $NaNO_2$ in acid solution. The —$CH_2C_6H_5$ group is removed by reduction in conventional manner.

As mentioned above, the compounds according to the invention are especially useful since they are effective for the inhibition of dental plaque and the removal of plaque already formed on the tooth surfaces For this reason the compounds according to the invention are valuable agents for keeping the tooth surfaces clean and, accordingly, also for the inhibition of dental caries, gingivitis and parondontitis.

The occurrence of dental caries and parodontitits appears to be the result of complex biological interactions of various microorganisms forming a part of the dental plaque, i.e. the deposit normally formed on the surfaces of the teeth. Chronic parodontitis, apparently the most common cause of tooth loss, is an inflammatory process of the supporting tissues of the teeth and about as prevalent as caries.

Formation of dental caries and parodontitis have a common cause, viz. the formation of dental plaque. The plaque is a deposit upon the tooth surface and contains primarily bacteria and saliva components. The structure of dental plaque changes from the soft initial stage to the formation of a harder and water-insoluble plaque which can cause caries as well as parondontitis. In an effort to maintain oral and dental hygiene a large variety of different substances are presently used. Such substances can be used in toothpastes, tablets, mouthwashes and the like.

A wide variety of chemical and biological agents have been suggested for the removal of dental plaque after it is once formed or for the inhibition of the formation of dental plaque. However, mechanical removal of dental plaque has hitherto been the most effective method. For the inhibition of dental plaque in other ways the use of different types of antibiotics, chemotherapeutical agents and disinfectants, fluorine compounds, organic phosphatases, chelate-forming agents, emulsifiers, etc. has been suggested. Examples of such agents are penicillin (antibiotic), chlorohexidine and 8-hydroxyquinoline (disinfectants), ethylenediamine tetraacetate (chelate-forming agent), NaF (strengthening of the tooth enamel).

Some of these previously suggested agents have exhibited insignificant effects. Others such as antiseptic and antibiotic agents can certainly be effective but often cause side effects which must be considered worse than the condition removed.

It is now clear that the causes of the plaque-formation are of a very complicated nature, and for the chemical removal thereof it has been found necessary to employ compounds of a very specific chemical structure. To be useful for this purpose the compounds must have properties such as a low antibacterial effect, very low toxicity and lack undesired side effects such as discoloration of the tooth enamel.

The compounds according to the invention have been submitted to comprehensive toxicological and teratological tests and it has been found that their toxical and antibacterial effects are so low that the normal microflora in the oral cavity is not disturbed. The compounds show a slight anti-inflammatory effect but no teratological side effects have been found in the compounds of the present invention.

The compounds according to the invention have been submitted to intensive in vitro and in vivo tests and compared with reference substances which have been or are clinically used. The in vitro tests were performed in an artificial mouth using extracted teeth.

Artificial mouth

The plaque-inhibiting effect was studied in a specially constructed artificial mouth, originally described by Pigman et al. in J. Dent. Res. 31, 627, 1952, and later modified by Naylor et al. (cf. "Dental Plaque", 1969).

Figure 1:
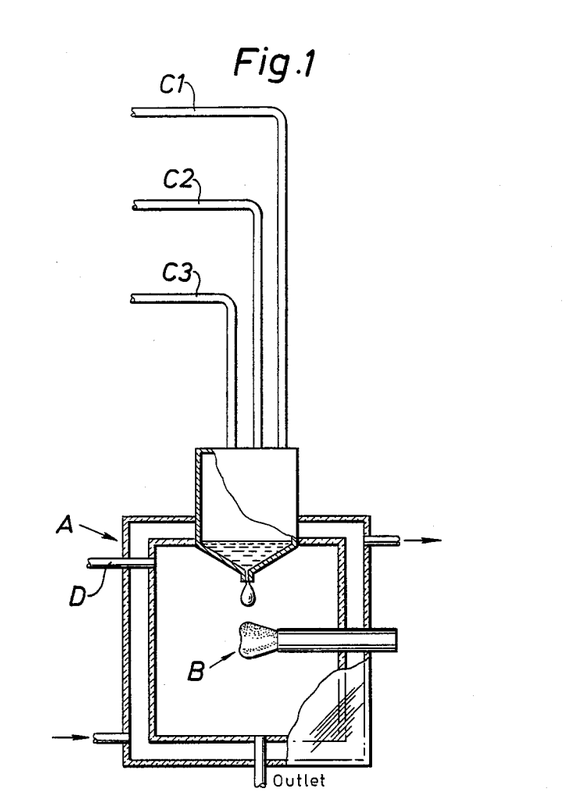

The apparatus used for the experiments is described in detail with reference to the enclosed FIG. 1. It consists of a jacketed glass chamber provided with an inlet opening to which several tubes are connected (D, C1, C2, C3). One or two extracted human teeth are introduced into the chamber mounted on glass tubes as shown in FIG. 1 (B). By means of peristaltic pumps slow-moving flows (C1, C2, C3) of substrate, bacteria (Streptococcus mutans) and sterile saliva are supplied to a mixing chamber from which the mixture is dropped onto the tooth surfaces. The interior of the chamber, in which the tooth or the teeth are placed, is maintained at a slight superatmospheric pressure achieved with a gas flow of carbon dioxide and nitrogen through the tube D. The temperature inside the vessel is maintained constant at 35° C. by means of a water flow circulating in the chamber jacket. To facilitate the tests, several similar apparatuses can be connected in series.

After a period of 3-4 days, a tooth introduced into the chamber exhibited a plaque deposit on the surface. This plaque deposit consists of saliva components, cellular fragments and bacteria. By removing a mounted tooth at certain intervals from the beginning of the test and treating it with different substances the ability of said substances to inhibit the formation of plaque, i.e. the plaque-inhibiting effect of the compounds can be estimated.

Figure 2:
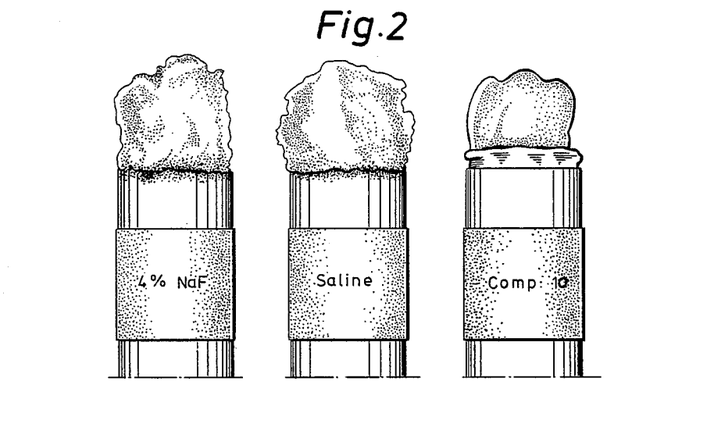

The compounds according to the present invention were tested as indicated above and showed a marked plaque inhibiting effect which was significantly higher than that obtained with a bactericide such as chlorohexidine. Chlorohexidine has an antiseptic activity but also other undesired effects such as discoloration of the tooth surface and development of bacterial resistance by continuous use. Test results obtained with the compounds of the invention indicate that no plaque was formed even after fourteen days by the addition of saliva, nutrition medium and bacteria when treating the tooth surface twice a day. FIG. 2 shows typical results obtained after a treatment period of fourteen days in the apparatus described in FIG. 1, i.e. under continuous dropwise addition of saliva, nutrition medium and bacteria, the test teeth having been treated twice a day with a 4% sodium fluoride solution, physiological saline, and a 1% solution of compound 10 according to the invention, respectively. As can be seen from FIG. 2, the tooth treated with compound 10 according to the invention is completely free from plaque formation, whereas the teeth treated with the 4% sodium fluoride solution and physiological saline exhibit a substantial plaque deposit.

Test in vivo

For the in vivo tests dogs have proved to be suitable experimental animals (Egelberg: Odont. Revy 16, 31-41, 1965).

The tests were performed by giving the dogs hard food and several tooth-cleanings during a period of fourteen days, as a result of which the dogs obtained a very good tooth status, i.e., clean teeth without caries. Gingival pockets and other membrane surfaces of the oral cavity were clinically without objection.

After said treatment the test was begun. The dogs were now given soft food and the tooth-cleaning was eliminated, thereby creating favorable conditions for plaque formation. By painting the teeth at one time with the compounds according to the invention, e.g. compound 10 or others, and at another time with physiological saline, the degree of plaque inhibition could be observed.

Figure 3:
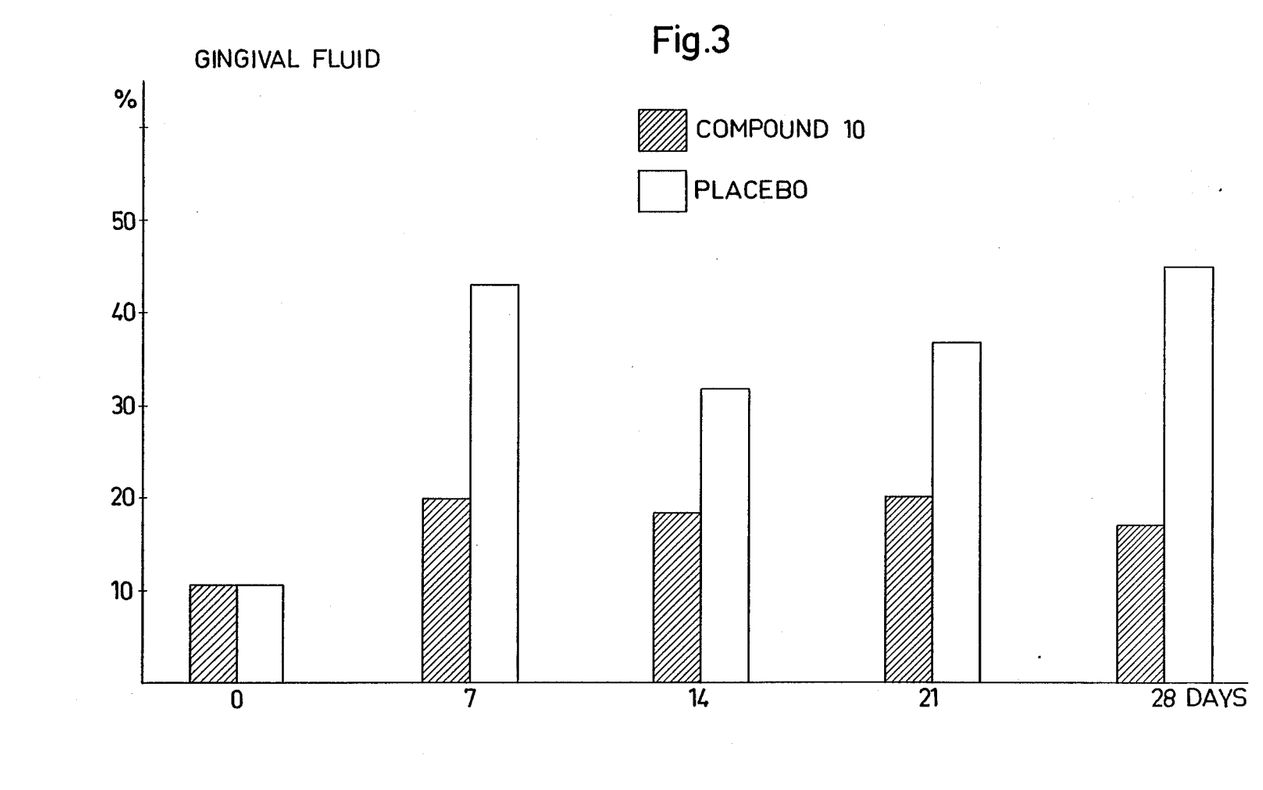

Another way to record plaque formation is to estimate, quantitatively, the increase of gingival fluid in the gingival pockets. Plaque formation causes an increase in the secretion of gingival fluid (cf. Attstrom et al.: J. Periodont. Res., Preprint 1971). The results obtained in these experiments are diagrammatically shown in FIG. 3. As can be seen from FIG. 3, an essential decrease of gingival fluid was obtained with compound 10 according to the invention as compared to placebo experiments.

The effect of the compounds has been studied according to the method described above in which the tooth surfaces of the dogs were painted twice a day over a four-week period. A control group of the same dogs was treated parallelly with physiological saline. The visual as well as quantitative estimations of the status of the teeth after the end of the treatment period showed that the teeth treated with compound 10 had a significantly lower formation of plaque than the control teeth (see FIG. 2).

The cause of the very marked plaque-decreasing effect of the compounds according to the invention is not completely clear but it is believed that the novel compounds tend to give a low surface tension to the tooth surface deteriorating the binding of the plaque to the tooth surface. However, the invention is not limited to any specific explanation of the effect obtained. Further, it has been found that some of the compounds according to the present invention have a greater effect than others, and it is presumed that this may be caused by the fact that the less effective compounds are more easily removed from the tooth surface than those which have been found to be more effective. The estimation of the effect of the compounds is based on application of the compounds twice a day, which is regarded to correspond to commonly occurring tooth cleaning frequency, e.g. brushing of the teeth morning and night. Another factor of importance for the utility of the compounds of the invention for the intended purposes is their solubility in water. Certain compounds are more soluble than others and it is preferred to use compounds having a solubility corresponding to or exceeding about 1% by weight.

The novel compounds according to the present invention are suitably prepared and tested in the form of the hydrochlorides or hydrofluorides. Said salts are also preferably used in commonly occurring compositions for the cleaning of teeth and the oral cavity, although the bases per se or other pharmacologically acceptable salts can be used. The salts can be prepared from the bases in a manner known per se. Suitable salts include those of maleic acid, malic acid and succinic acid.

Preferred compositions in which the compounds according to the invention can be used in the form of additives are toothpastes or tooth powders, mouth rinses, mouth spray preparations, chewing gum, tablets, etc. In such products the compounds according to the invention can be used in concentrations from 0.1 to 5%, calculated on the weight of the total composition, and they can also be used together with other pharmacologically active substances such as sodium fluoride, 6-n-amyl-m-cresol or 2,4-dichlorobenzyl alcohol.

The invention is further elucidated by the following specific examples.

EXAMPLE 1

3-(4-propyl-heptyl)morpholine 46.6 grams (0.16 mole) of 6-propyl-2-benzylamino-1-nonanol and 11 grams (0.20 moles) of ethylene oxide in 200 ml. 96% ethanol were kept at 100° C. in an autoclave with careful stirring for three hours. The reaction mixture was evaporated. 57 grams (100%) of GLC-unitary substance were obtained, viz. N-(2-hydroxyethyl)-6-propyl-2-benzylamino-1nonanol. Said 57 grams were dissolved in 450 ml. of 70% (w/w) sulfuric acid and kept in a glass autoclave at 140°-150° C. for 15 hours. The reaction mixture was admixed with an excess of 40% aqueous NaOH and extracted with diethyl ether. The ether extract was dried over sodium sulphate and evaporated. Distillation gave 49.7 grams (93 %) N-benzyl-3-(4-propylheptyl)morpholine, boiling point 163°-165° C./0.01mm Hg. This substance (49.7 grams) and 3 grams of 10% (w/w) Pd-C in 500 ml. 96% ethanol were hydrogenated in a steel autoclave at 100° C. and 100 atmospheres hydrogen pressure for 12 hours. Conventional processing gave 34.2 grams (96%) of 3-(4-propylheptyl)morpholine, boiling point 76°-78° C./0.01 mm Hg. The base obtained was dissolved in ether and the hydrochloride precipitated with hydrochloric acid in ethanol. Recrystallization gave crystals having a melting point of 118°-119° C.

EXAMPLE 2

3-(4-propyl-heptyl)-4-(5-hydroxypentyl)morpholine

A mixture of 8.0 grams (0.035 moles) of 3-(4-propylheptyl)-morpholine, 4 grams of triethylamine, 5.8 grams (0.035 moles) of glutaric acid-monomethylesterchloride and 100 ml. of benzene were refluxed for 3 hours. After cooling the triethylamine hydrochloride formed was removed by filtration and the benzene solution was directly admixed with 12 grams of lithium aluminum hydride in 500 ml of ether. The reaction mixture was refluxed for 8 hours and decomposed by slow addition of water and sodium hydroxide. The precipitate was filtered off. The ether solution was dried and evaporated to dryness and the residue was distilled at 144°-146° C./ 0.01 mm Hg.; yield 9.8 grams (89%). The base obtained was dissolved in ether and the hydrochloride precipitated with hydrochloric acid in ethanol. After recrystallization from ethylacetate/ether, the melting point was 59°-60° C.

EXAMPLES

Further Examples 3-13 were prepared pursuant to the process described in Example 2, while Examples 14 and 15 were prepared as described immediately after Table I below. The compounds were tested in accordance with the "Artificial Mouth" procedure described hereinbefore. The estimated plaque-inhibiting effect of each of the examples is reported in Table I along with its respective compound.

TABLE I

Effect $$\text{morpholine ring with } O, N-R_2, R_1$$

| | $R_1$ | $R_2$ | Melting point of the hydrochloride °C. | Plaque Inhibiting Effect* |
|---|---|---|---|---|
| 2. | 3-$CH_2CH_2CH_2CH(CH_2CH_2CH_3)(CH_2CH_2CH_3)$ | —$(CH_2)_5OH$ | 59–60° C. | +++ |
| 3. | 3-$CH_2CH_2CH_2CH(CH_2CH_2CH_3)(CH_2CH_2CH_3)$ | —$(CH_2)_6OH$ | Base b.p. 141–143/0,01 mm Hg | +++ |
| 4. | 3-$CH_2(CH_2)_6CH_3$ | —$(CH_2)_5OH$ | 98–99 | +++ |
| 5. | 3-$CH_2(CH_2)_6CH_3$ | —$(CH_2)_6OH$ | Base b.p. 140–142/0,01 mm Hg $n_D^{20} = 1.4735$ | ++ |
| 6. | 3-$CH_2(CH_2)_8CH_3$ | —$(CH_2)_5OH$ | 107–109 | ++ |
| 7. | 3-$CH_2(CH_2)_8CH_3$ | —$(CH_2)_6OH$ | Base b.p. 157–159/0,01 mm Hg $n_D^{20} = 1.4730$ | ++ |
| 8. | 2-$CH_2(CH_2)_8CH_3$ | —$(CH_2)_5OH$ | 126–127 | ++ |
| 9. | 2-$CH_2(CH_2)_6CH_3$ | —$(CH_2)_3OH$ | 127–129 | (+) |
| 10. | 3-$CH_2CH_2CH_2CH(CH_2CH_2CH_3)(CH_2CH_2CH_3)$ | —$(CH_2)_2OH$ | 70–72 | +++ |
| 11. | 2-$(CH_2)_9CH_3$ | —$(CH_2)_2OH$ | 120–122 | +++ |
| 12. | 2-$(CH_2)_9CH_3$ | —$(CH_2)_3OH$ | 126–128 | +++ |
| 13. | 2-$(CH_2)_9CH_3$ | —$(CH_2)_4OH$ | 125–127 | +++ |
| 14. | 3-$CH_2CH_2CH_2CH(CH_2CH_2CH_3)(CH_2CH_2CH_3)$ | —$(CH_2)_3OH$ | Base b.p. 122–124/0,01 mm Hg | +++ |
| 15. | 2-$(CH_2)_7CH_3$ | —$(CH_2)_5OH$ | Base b.p. 128–130/0,01 mm Hg | ++ |

*+++ = very good activity
++ = good activity
+ = fairly good activity
(+) = weak activity

EXAMPLE 14
3-(4-propyl-heptyl)-4-(3-hydroxypropyl)morpholine

A mixture of 22.7 grams (0.1 mole) of 3-(4-propylheptyl)morpholine, 6.4 grams (0.11 moles) trimethyleneoxide and 150 ml. 96% ethanol was kept at 150°–200° C. for 15 hours in an autoclave. Distillation of the reaction mixture gave 24.6 g (86%) of 3-(4-propyl-heptyl)-4-(3-hydroxypropyl)morpholine), boiling point 122°–124° C./0.01 mm Hg.

EXAMPLE 15
2-octyl-4-(5-hydroxypentyl)-morpholine 20.0 grams (0.1 mole) 2-octylmorpholine, 13 grams (0.1 mole) of 5-chloropentanol and 12 grams of triethylamine in 150 ml. toluene were kept at 140°–150° C. for 12 hours in an autoclave. After cooling, the organic phase was washed twice with water, dried, and the solvent was evaporated and the base distilled at 128° C./0.01 mm Hg.; yield: 22.0 grams (77%).

The base obtained was dissolved in ether and the hydrochloride was precipitated with hydrochloric acid in ethanol. After recrystallization from ethylacetate/ether, the melting point was 122°–123° C.

EXAMPLE 16.

| Tooth paste Components | % by weight |
|---|---|
| Compound according to Example 10 | 1 |
| Dicalciumphosphate | 50 |
| Sorbitol | 6 |
| Glycerin | 18 |
| Na—carboxymethylcellulosa | 2 |
| Na—laurylsulphate | 1 |
| Na—saccharin | 0.1 |
| Peppermint oil | 0.9 |
| Water | up to 100 |

EXAMPLE 17

| Chewing gum | % by weight |
|---|---|
| Center | |
| Compound according to Example 2 | 3 |

| Chewing gum | % by weight |
|---|---|
| Fructose | 50 |
| Glycerin | 5 |
| Mannitol | 30 |
| Gum base | 2 |
| Carboxymethylcellulosa | 10 |
| Sodium cyclamate | 1 |
| Coating | |
| Carnauba wax containing | |
| Fructose | 9 |
| Gum arabic | 5 |
| Dextrin | 2 |
| Flavor | 2 |

The center composition was mixed at 50° C.

EXAMPLE 18

| A chewable tablet | grams |
|---|---|
| A mixture of | |
| Compound according to Example 3 | 10 |
| Compound according to Example 11 | 10 |
| Sorbitol | 800 |
| Potato starch | 150 |
| Gelatin, 5% aqueous solution | 30 |
| Peppermint oil | — |
| Sodium cyclamate | 2 |
| *Sodium saccharin | 1 |

Was tabletted to produce 1000 tablets containing 1% of the compound of Example 3 and 1% of the compound of Example 4.

EXAMPLE 19

| Mouth Rinse Liquid | % by weight |
|---|---|
| Compound according to Example 2 | 1 |
| Glycerin | 10 |
| Ethanol | 15 |
| Tween 80 (surfactant) | 0.1 |
| Sodium cyclamate | 1.0 |
| Sodium saccharin | 0.1 |
| Menthol flavor | 0.1 |
| Water | up to 100 |

We claim:

1. Method of keeping the oral cavity and the surfaces of the teeth free from plaque or removing plaque already formed by treating the oral cavity and especially the surface of the teeth with a compound having the general formula

I wherein $R_1$ is a straight or branched alkyl group containing 8 to 10 carbon atoms at the 2- or 3-position of the morpholino ring, and $R_2$ is a straight or branched alkyl group containing 2 to 6 carbon atoms, substituted with a hydroxy group except in the alpha-position, the sum of the carbon atoms in the groups $R_1$ and $R_2$ being 12 to 16; and pharmaceutically acceptable salts thereof, in an aqueous solution or in a composition containing the same.

2. A method as in claim 1 in which said compound is 3-(4-propyl-heptyl) -4-(2-hydroxyethyl) morpholine.

* * * * *

UNITED STATES PATENT AND TRADEMARK OFFICE
CERTIFICATE OF CORRECTION

PATENT NO. : 4,894,221

DATED : January 16, 1990

INVENTOR(S) : Sven E. Hernestam, et al.

It is certified that error appears in the above-identified patent and that said Letters Patent is hereby corrected as shown below:

Column 1, line 28: "to 16" should read as --8 to 16--

Column 1, lines 65-66: "or an hydroxyl group present in $R_2$ is a reactive oxide;" should read as --or an organic sölfonic ester, or wherein X together with a hydroxyl group present in $R_2$ is a reactive oxide;"

Column 2, line 27: "$R_2$ pl is" should read as --$R_2$ is--

Column 2, lines 40-4L: "straight branched" should read as --straight or branched--

Column 2, line 50: "$(CH_2)_n-COOC2H_5$" should read as --$(CH_2)_n-COOC_2H_5$--

Column 2, line 63: "R" should read as --$R_4$--

Column 2, line 66: "-CH" should read as -- $-CH_2C_6H_5$ --

UNITED STATES PATENT AND TRADEMARK OFFICE
CERTIFICATE OF CORRECTION

PATENT NO. : 4,894,221

DATED : January 16, 1990

INVENTOR(S) : Sven E. Hernestam, et al.

It is certified that error appears in the above-identified patent and that said Letters Patent is hereby corrected as shown below:

Column 4, line 58: "surfaces For" should read as --surfaces. For--

Column 8, line 12: "lnonanol." should read as --1-nonanol.--

Signed and Sealed this

Thirty-first Day of December, 1991

Attest:

HARRY F. MANBECK, JR.

*Attesting Officer*  *Commissioner of Patents and Trademarks*